United States Patent [19]

Binder

[11] Patent Number: 4,969,901
[45] Date of Patent: Nov. 13, 1990

[54] PLASTIC SURGERY IMPLANT

[76] Inventor: William J. Binder, 9201 West Sunset Blvd., Los Angeles, Calif. 90069

[21] Appl. No.: 345,986

[22] Filed: May 2, 1989

Related U.S. Application Data

[63] Continuation-in-part of Ser. No. 212,616, Jun. 28, 1988, abandoned.

[51] Int. Cl.$^5$ ............................ A61F 2/02; A61F 2/28
[52] U.S. Cl. ........................................ 623/11; 623/16; D24/33
[58] Field of Search ........................ 623/11, 16, 8, 66; D24/33; 128/DIG. 21

[56] References Cited

U.S. PATENT DOCUMENTS

| D. 290,877 | 7/1987 | Giampapa et al. | D24/33 |
| D. 290,878 | 7/1987 | Giampapa et al. | D24/33 |
| D. 290,879 | 7/1987 | Giampapa et al. | D24/33 |
| 4,344,191 | 8/1982 | Wagner | 623/16 |
| 4,790,849 | 12/1988 | Terino | 623/11 |

FOREIGN PATENT DOCUMENTS

| 2040688 | 1/1979 | United Kingdom | 623/8 |

Primary Examiner—Alan W. Cannon
Attorney, Agent, or Firm—Christie, Parker & Hale

[57] ABSTRACT

An improved implant for the mid-facial or submalar region of a patient's face. The implant is relatively thin with a teardrop-shaped profile. It has a relatively broad head which is adapted to fit in the canine fossa of the maxillary bone, and a tapered, relatively narrow tail which extends laterally under the zygomatic eminence. The implant is anatomically correct to create the appearance of soft tissue restoration without distorting the normal facial bone structure. In addition, it softens prominent nasolabial folds, and provides a more youthful looking fullness to the cheeks by repositioning and augmenting soft tissue which has lost the underlying support of an atrophied fat pad of the cheeks.

6 Claims, 5 Drawing Sheets

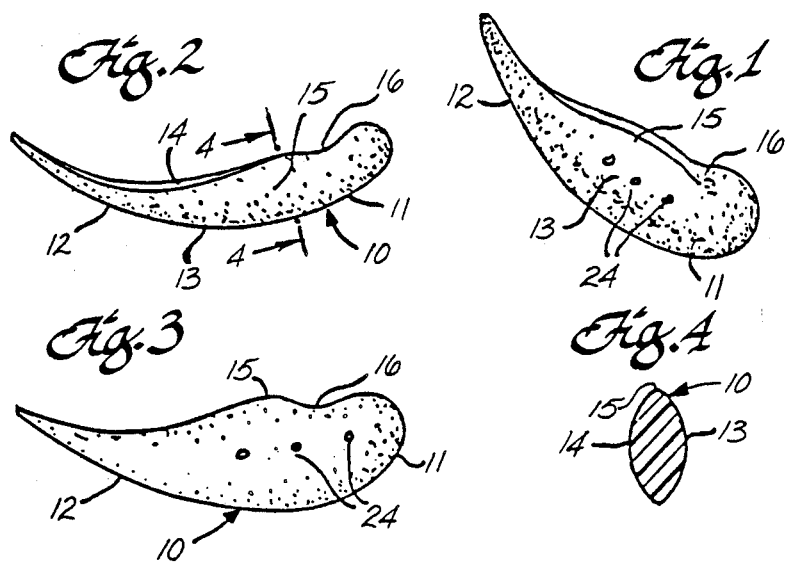
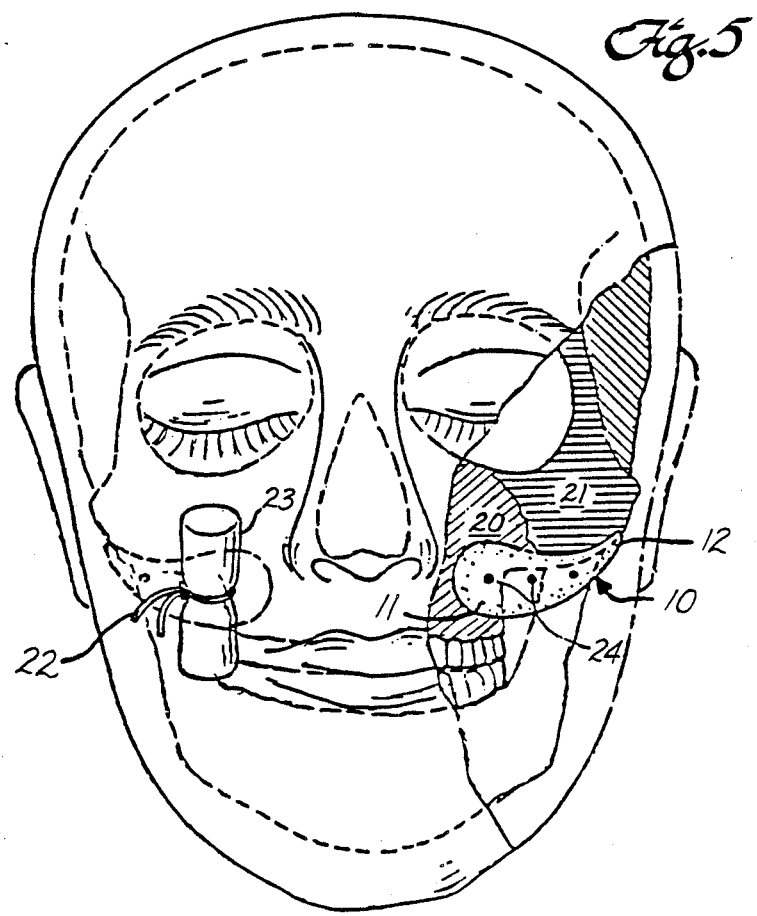

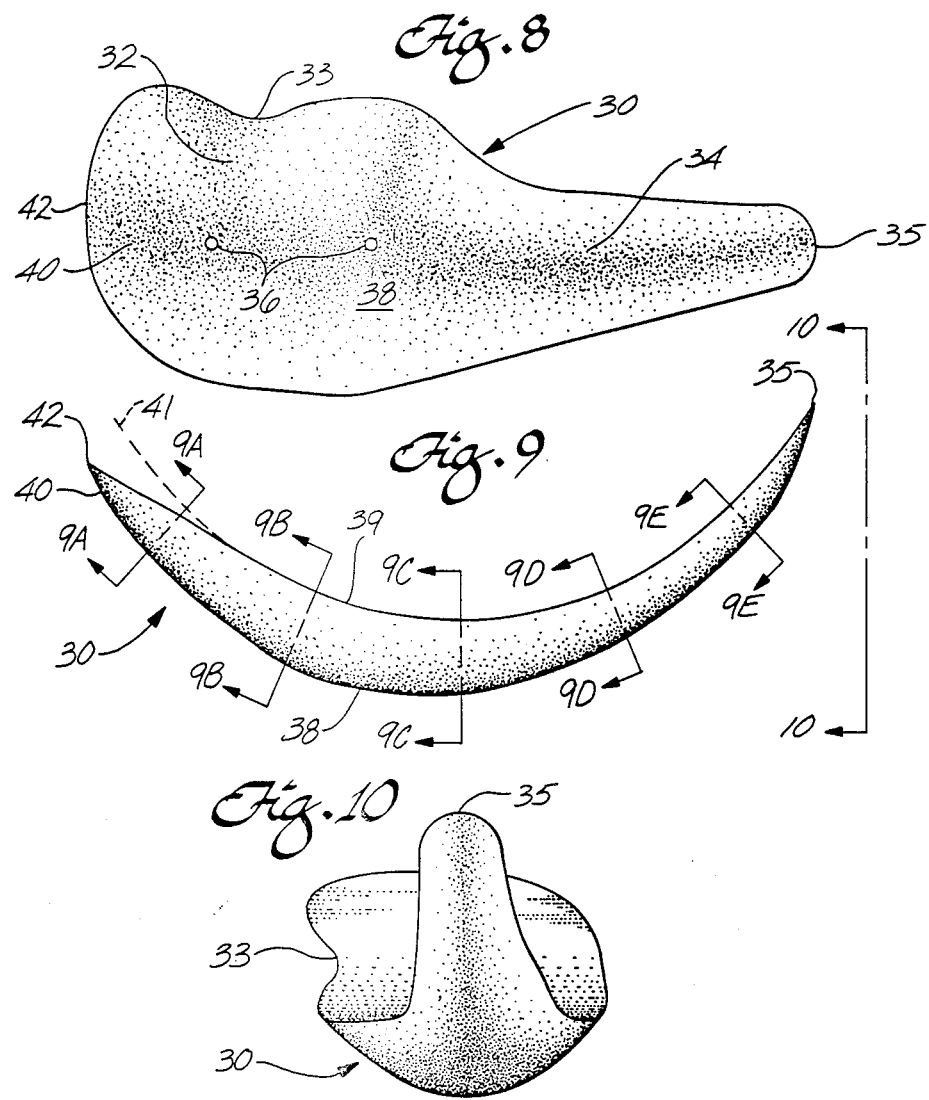

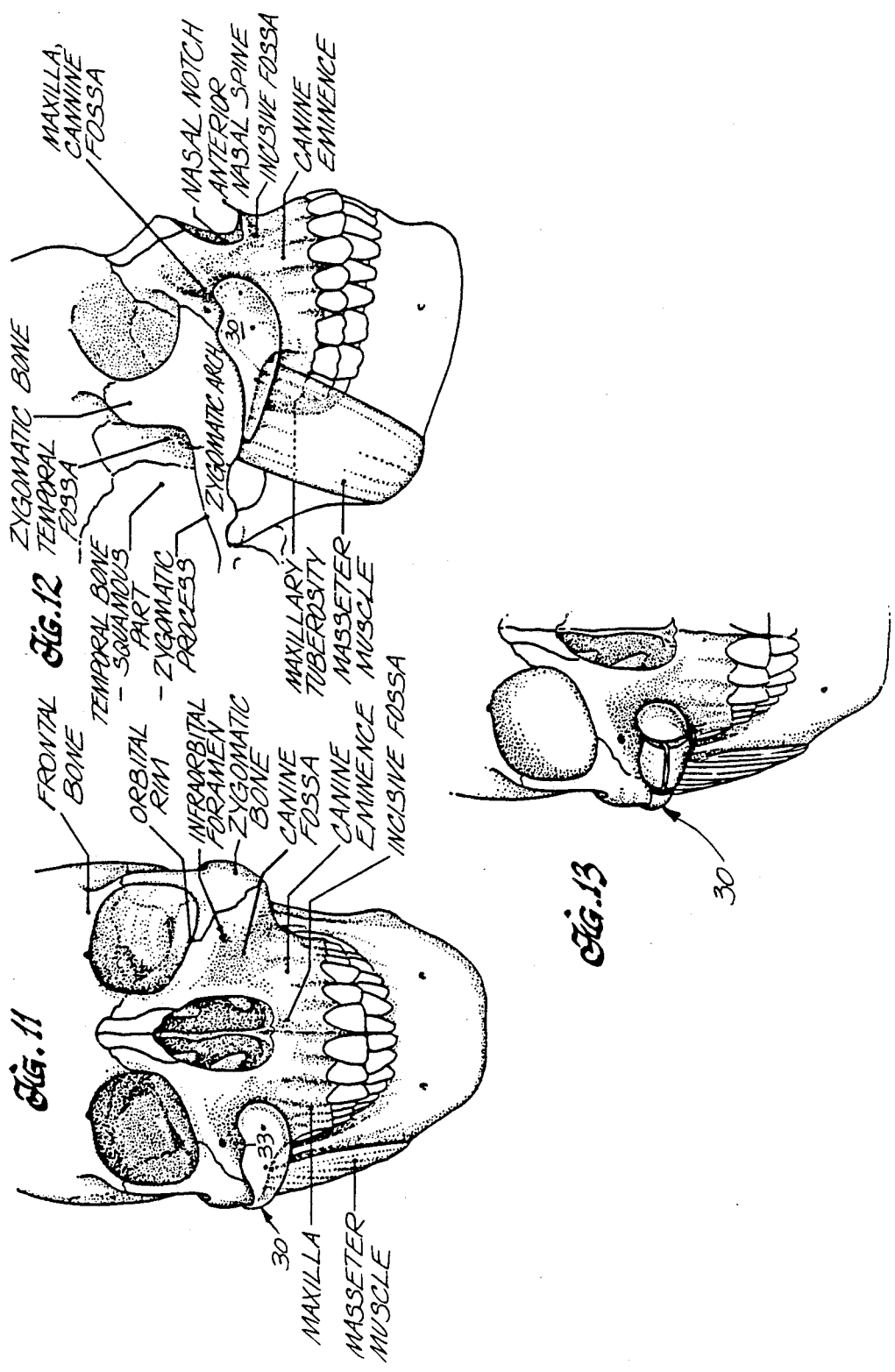

PLASTIC SURGERY IMPLANT

CROSS-REFERENCE TO RELATED APPLICATION

This is a continuation-in-part of U.S. Patent Application No. 07/212,616 filed June 28, 1988, now abandoned.

BACKGROUND OF THE INVENTION

This invention generally relates to the field of reconstructive and cosmetic surgery in the facial region.

As a person ages, the subcutaneous tissue and buccal fat pad in the face thins and no longer provides adequate support for the overlying skin. As a result, the overlying skin begins to sag, forming wrinkles, depressed areas and the like. A wide variety of surgical procedures have been developed over the years to tighten loose skin, and to augment depressed areas to provide a more youthful appearance. Similar types of surgical procedures have been developed to reconstruct congenital and trauma-caused deformities.

Nasolabial folds, which become more pronounced as a person ages due to the thinning of the underlying tissue, have provided a formidable challenge to even highly skilled surgeons to reduce the pronounced character of the folds, without the elimination thereof. Surgical incisions into or about the folds tend to leave visible scars. Face lifts tend to pull the overlying skin of the folds too tightly, thus eliminating soft, youthful looking nasolabial folds.

Malar implants which are used to augment cheekbones also tend to flatten out the nasolabial folds and to accentuate depressed mid-facial submalar areas of the face. As used herein, the term "submalar" refers to the medial mid-third region of the face which includes the canine fossa, the anterior face of the maxilla, the subzygomatic area, and the surface extending laterally beneath the zygomatic arch.

Further background information relating to cosmetic or reconstructive surgery in the mid-facial region can be found in the following publications which are incorporated herein by reference.

Brennan, G. H., "Augmentation Malarplasty" *Arch. Otolaryngol*, Vol. 108, July 1982, pp. 441-444.

Guerrerosantos, J., "Recontouring of the Middle Third of the Face with Onlay Cartilage Plus Free Facial Graft," *Annals of Plastic Surgery*, Vol. 18, No. 5, May 1987, pp. 409-420.

Kent, J. N., et al., "Chin and Zygomatico-Maxillary Augmentation with Proplast: Long Term Follow-up," *J. Oral Surgery*, Vol. 39, Nov. 1981, pp. 912-919.

Lawson, W., et al., "Malar Implants for Restoration of Facial Contour," *Aesthetic Surgery*, pp. 173-179.

Greenwald, A. E., "Malar Augmentation-High Cheekbones," read before American Society of Cosmetic Surgeons, Jan. 13, 1984, pp. 29-35.

Millard, D. R., et al., "A Challenge to the Undefeated Nasolabial Folds," *Plastic and Reconstructive Surgery*, July 1987, pp. 37-44.

Newman, J., et al., "Retrograde Suspension Malarplasty," *The American Journal of Cosmetic Surgery*, Vol. 3, No. 3, 1986, pp. 7-12.

Tobin, H.A., "Malar Augmentation as an Adjunct to Facial Cosmetic Surgery, *The American Journal of Cosmetic Surgery*," Vol. 3, No. 3, 1986, pp. 13-16.

Whitaker, L. A., "Aesthetic Augmentation of the Malar-Midface Structures," *Plastic and Reconstructive Surgery*, Sept. 1987, pp. 337-346.

Wilkinson, T. S., "Complications in Aesthetic Malar Augmentation," *Plastic and Reconstructive Surgery*, May 1983, pp. 643-649.

What has been needed and heretofore unavailable is an effective means of reducing the prominence of nasolabial folds, yet provide a full, natural, more youthful appearance. The present invention satisfies that need.

SUMMARY OF THE INVENTION

The present invention is directed to a facial implant, particularly a facial implant which can provide a more natural fullness to the submalar region of a person's face which in turn can moderate the prominence of nasolabial folds.

The facial implant in accordance with the present invention generally has a relatively thin body with a teardrop-shaped profile. The body has a relatively broad head portion and a more narrow tapered tail section. In one form, the posterior and anterior faces of the implant are slightly convex, and the implant is anatomically curved around an arc to facilitate correct fitting of the implant against the supporting facial bones of the patient upon implantation. Additionally, the upper or superior edge of the implant is provided with a recess to accommodate the infraorbital nerve. The tail of the implant preferably tapers posteriorly to facilitate proper placement immediately under the zygomatic eminence.

The implant of the invention is most advantageously inserted into a subcutaneous surgically formed pocket in the mid-facial or submalar region of the patient through an intraoral, Caldwell Luc approach. The enlarged head of the implant is placed within the canine fossa region of the maxillary bone with the tapered tail thereof extending laterally underneath the eminence of the zygomatic bone. The implant is secured by a suture which passes through holes in the body of the implant and the overlying tissue, and which are tied to a pad such as a dental roll on the exterior of the cheek. The implant is fixed within the subcutaneous pocket so that the sutures can be removed in about three days to avoid noticeable scarring of the overlying tissue.

The implant is made of material which is compatible with the body tissue and fluid it contacts. Silicone plastics such as Silastic have been found to be particularly suitable.

The implant of the invention when properly positioned augments tissue deficiencies which result from aging. It adds fullness to the submalar region of a patient's face to provide a more youthful appearance. Moreover, it can substantially reduce the prominence of the nasolabial folds. The implant can be used alone or in conjunction with other reconstructive or cosmetic surgery.

These and other features of the invention will become more apparent from the following detailed description of the invention when taken in conjunction with the accompanying exemplary drawings.

BRIEF DESCRIPTION OF THE DRAWINGS

FIG. 1 is a perspective view of an implant embodying features of the invention with the anterior surface presented;

FIG. 2 is a top view of the implant shown in FIG. 1;

FIG. 3 is a front view of the implant shown in FIG. 1 with the anterior surface presented;

FIG. 4 is a transverse cross-sectional view taken along the lines 4—4 shown in FIG. 2;

FIG. 5 is a front view of a human face, with underlying bone structure partially exposed, illustrating the placement of implants embodying features of the invention;

FIG. 8 is a front view of a second embodiment of the implant;

FIG. 9 is a top view of the implant shown in FIG. 8;

FIG. 10 is an end view on lines 10—10 of FIG. 9;

FIGS. 11 and 12 are front and side views respectively of a human skull, and showing the anatomical positioning of an implant according to the invention; and FIG. 13 is a view similar to FIG. 11, but showing only a portion of the skull, and with the implant partly broken away.

DETAILED DESCRIPTION OF THE INVENTION

Figure 6:
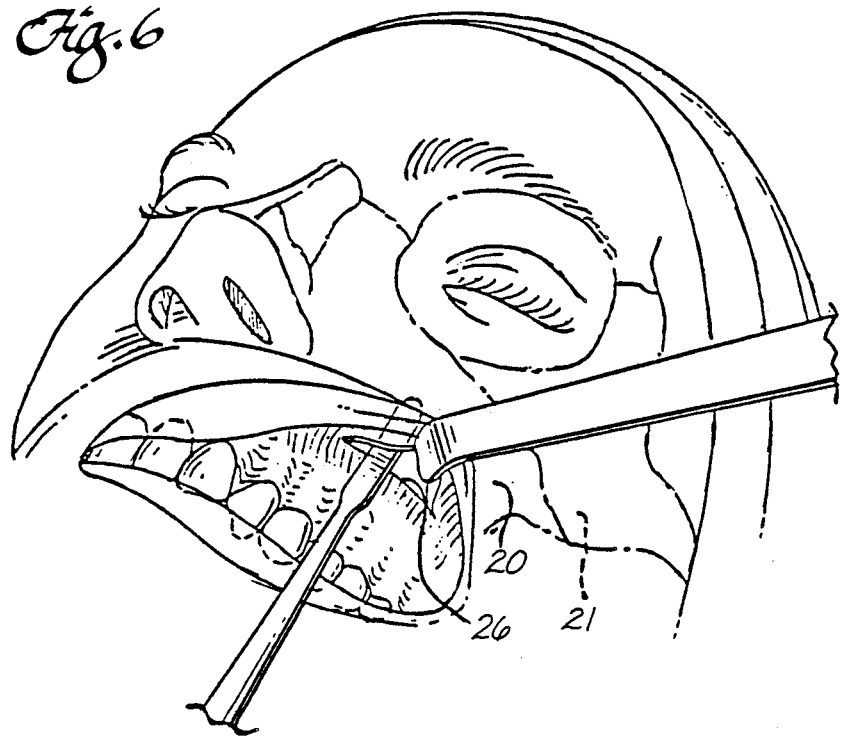
FIGS. 6 and 7 are oblique views of a patient illustrating the intraoral Caldwell Luc approach for inserting an implant embodying features of the invention.

A facial implant 10 shown in FIG. 1 which embodies features of the invention generally has a thin, relatively flat body with a teardrop-shaped profile. The implant 10 comprises a relatively broad head section 11 and a relatively narrow tapered tail section 12. Anterior face 13 and posterior face 14 of the implant body 10 are slightly convex, as shown in FIG. 4. The implant body 10 preferably is preformed to curve longitudinally in the posterior direction, as shown more clearly in FIG. 2, to facilitate a better fit with underlying supporting bone structure. The upper or superior edge 15 of the implant has a recess 16 to accommodate the infraorbital nerve.

In FIG. 5, the implant 10 is shown properly positioned in the patient's left submalar region with the head 11 placed in the canine fossa of maxillary bone 20 with the tapered tail section 12 extending laterally under the eminence of the zygomatic bone 21. The right side of the face shown in FIG. 5 illustrates the temporary immobilization of an implant 10 by means of suture 22 and dental roll 23 which is used as a bolster. The suture 22 passes through fenestrations or holes 24 provided in the implant body 10 and through the cheek and is tied about the dental roll 23.

The dimensions of the implant will vary depending upon anatomical requirements of the patient and the amount of augmentation needed. Typically, however, the overall length of the implant may range from about 4 to 8 cm, the maximum width of the head section at the widest portion may range from about 1.3 to about 3 cm, and the maximum thickness in the mid-section thereof may range from about 2 to about 8 mm. The tip of the head section may vary in thickness from about 1.25 to about 3 mm.

Figure 7:
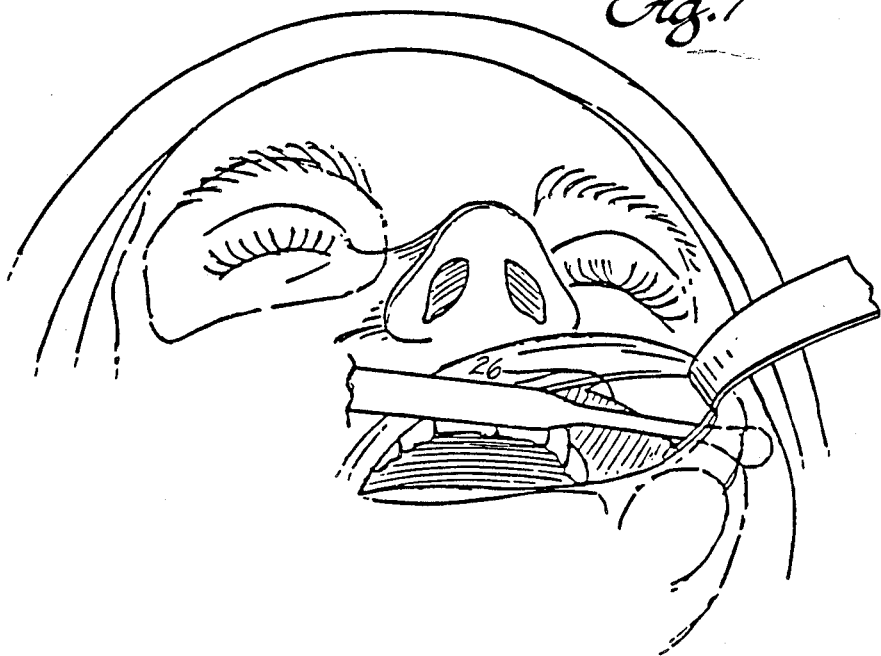
Figure 9A:
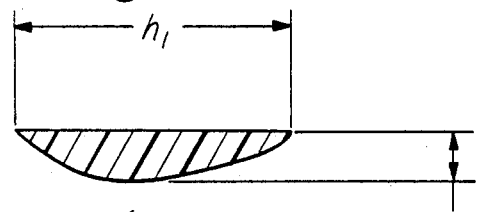
FIGS. 9A-9E are cross-sectional views as identified on FIG. 9.
Figure 9B:
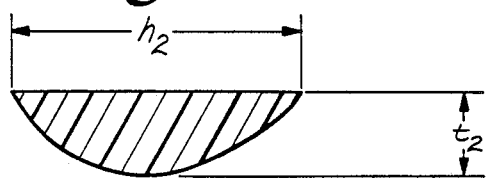
Figure 9C:
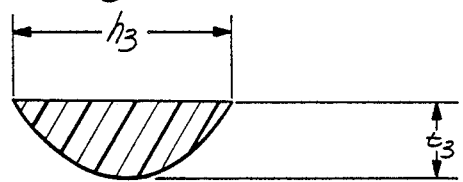
Figure 9D:
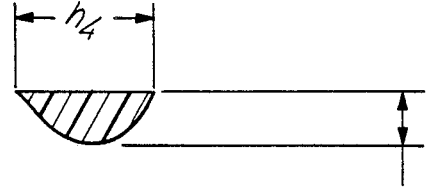
Figure 9E:
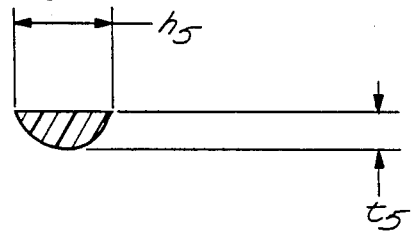

FIGS. 6 and 7 illustrate the preparation of the midfacial and sublabial areas of a patient for the insertion and placement of the implant. Initially, the suborbital maxillary, zygomatic, and sublabial areas of the patient's face are infiltrated with suitable local anesthetic, such as a 1% lidocaine solution. As depicted in FIG. 6, a small incision 26 is made into the left canine fossa. Through a standard Caldwell Luc approach, incision 26 is made through the periosteum to the underlying maxillary bone 20. The periosteum is elevated superiorly to the infraorbital rim and over the face of maxilla 20. The dissection should be extended medially a short distance, but it should not approach the piriform aperture.

The dissection is continued over the zygomatic-subzygomatic regions of the face, as shown in FIG. 7, to provide more complete exposure of the premaxillary and maxillary areas of the mid-face or submalar region of the patient. As the pocket is expanded laterally over the zygoma and maxilla, a supraperiosteal dissection can be employed. It is easier, and prevents post-operative tenderness. Ligaments or soft-tissue attachments to the underlying bone structure are incised and unroofed to form a subcutaneous pocket adapted to receive the implant between the periosteum and underlying bone structure in the facial area requiring augmentation.

An implant is used having the size and shape which will provide the desired augmentation. Before the implant is inserted into the subcutaneous pocket, the overlying skin is marked to correspond to the fenestrations 24 in the implant which will properly position the implant. Needles having suture material 22 connected thereto are first passed through two fenestrations or holes 24 provided in the implant body 10, and then through the skin overlying the subcutaneous pocket where marked.

The implant 10 is inserted into the surgically formed subcutaneous pocket in the desired position and the suture 22 is tied externally about a bolster such as a dental roll 23, thereby securing and immobilizing the implant in the desired position. The intraoral incision may then be repaired. After about three days, the surrounding tissues are able to fix the implant sufficiently within the subcutaneous pocket so that the suture material 22 holding the implant in place can be removed.

A second and presently preferred embodiment of the invention is shown in FIGS. 8-10 illustrating an implant 30 configured for the left side of the face. While similar in many respects to the embodiment already described, implant 30 is an elongated strip of generally plano-convex or circular-segment cross section as contrasted with the roughly biconvex section of implant 10.

Referring to FIGS. 8-10, implant 30 has an enlarged anterior or head section or portion 32, the upper or superior edge surface of which defines a recess or depression 33 to provide clearance for the infraorbital nerve. Extending distally from head portion 32 is a tail section or portion 34 which tapers (reduces in both height and thickness) to a distal tip 35. A pair of holes 36 are formed through the implant to enable the temporary anchoring or fixation procedure already described.

Implant 30 has an outer or anterior front surface 38 which is convex as shown in the sectional views of FIGS. 9A-E. An inner or posterior rear surface 39 of the implant is preferably generally flat or planar in cross section. The rear surface is concave when viewed from the top (FIG. 9) and of substantially constant radius, with the exception of a mesial end portion 40 which has an ever-increasing radius (dashed line 41 in FIG. 9 shows the constant radius, and the deviation of the mesial end portion). Mesial end portion 40 diminishes in both height and thickness toward a rounded mesial tip 42.

It has been determined that substantially all requirements can be met by four sizes of molded implants in the range of the following minimum and maximum dimensions:

a. The arc length of rear surface 39

(corresponding to the longitudinal dimension of the flattened implant) ranges from about 1⅝ inches to 2¾ inches.

b. The cross-sectional height and thickness dimensions, designated "h" and "t" in FIGS. 9A–E have the following minima and maxima (in inches) on the indicated section lines:

|  | Min. | Max. |  | Min. | Max. |
|---|---|---|---|---|---|
| $h_1$ | 0.547 | 0.875 | $t_1$ | 0.095 | 0.151 |
| $h_2$ | 0.561 | 0.898 | $t_2$ | 0.154 | 0.247 |
| $h_3$ | 0.445 | 0.711 | $t_3$ | 0.143 | 0.229 |
| $h_4$ | 0.273 | 0.437 | $t_4$ | 0.096 | 0.154 |
| $h_5$ | 0.193 | 0.309 | $t_5$ | 0.068 | 0.109 |

Two sizes intermediate these small and large implants will accommodate typical needs, but the dimensions can be scaled up or down as necessary for special cases.

The implant is preferably injection molded using a medical-grade silicone plastic (Dow-Corning "Silastic" is satisfactory). The mesial and distal ends are tapered to feather edges to form a smooth junction with the underlying bone.

FIGS. 11 and 12 illustrate the facial bones of the skull, and show an implant 30A (a mirror image of implant 30) as positioned on the right side of the facial midline. As shown, the head portion of implant 30A seats in and fills the maxillary canine fossa which is the most recessed or depressed part of the mid-facial skeleton. Mesial end portion 40 approaches, but terminates short of the nasal notch of the maxilla above the canine eminence. Depression 33 prevents unwanted interference with the infraorbital nerve (not shown) as already described.

The upper edge of the implant increases in height laterally of depression 33 to blend with the anterior-inferior orbital rim formed by the frontal, zygomatic and maxillary bones. The zygomatic process (the anterior part of the zygomatic arch) is a forwardly extending buttress generally paralleling the orbital rim. As the undersurface of this buttress curves rearwardly, it forms an easily palpable skeletal depression. The midsection of the implant seats in this depression and provides a smooth transition from the undersurface of the zygomatic buttress toward the maxillary tuberosity.

Implant tail portion 34 continues rearwardly beneath the zygomatic arch to a recessed area or groove at the tendinous insertions of the masseter muscle along the undersurface of the zygoma and over the infratemporal fossa. This portion of the implant provides a softly extended lateral profile for a desired high-cheekbone effect, and without overextension or accentuation of the zygomatic eminence or arch. To insure anatomical conformance, the upper edge of the implant descends abruptly at the junction of the head and tail portions, and at a greater downward angulation than the more gentle and relatively constant upward angulation of the lower edge.

The submalar positioning of the implant beneath the zygomatic arch restores a desired facial fullness which is lost in the normal aging process, primarily by atrophy and deterioration of the buccal fat pads which naturally provides such fullness in children and young adults. The implant enables facial rejuvenation with a relatively safe and simply intraoral implantation surgery which elevates and repositions sagging skin and soft tissue, and fills hollows and depressions to soften the nasolabial folds and restore fullness to the cheeks with adequately padded skin at healthy distension and elasticity.

This procedure has been very successful in augmenting submalar or cheek fullness to provide a more youthful appearance. In many younger patients (e.g., ages 38 to 50), it was found that subsequent to the implanting technique of the invention, there was no immediate need for face-lift surgery. In older patients, the implant provides additional structure which ensures a more successful face-lift, and reduces the need and frequency of secondary face-lift procedures commonly called "tuckup" procedures. Used in this manner, the procedure does not change the natural shape of the face.

When positioned in a more superior and lateral location, the implant can increase the projection over the malar complex, providing a more natural appearance to the "high cheekbone effect" than conventional malar augmentation procedures. There is little or no movement of the implant, and the feel thereof to the patient is natural. All procedures to date have been successful and patients who have received this procedure have found the results extremely satisfactory. No serious complications have occurred with this procedure. Two minor infections and four cases of asymmetry have occurred which have been effectively resolved without jeopardizing the success of the procedure.

While the description of the invention given herein has been directed to specific embodiments thereof, modifications and improvements can be made without departing from the scope thereof.

What is claimed is:

1. A facial implant for submalar placement, comprising an integrally molded and elongated curved strip of body-compatible plastic, the strip having a convex front surface and a concave rear surface, the front surface being convex in cross-section;

the strip having a head portion and a tail portion, the head portion having a generally central-thickened section which extends with reducing cross-sectional thickness to a thin mesial end portion, and the tail portion extending distally with reducing and tapering cross-sectional height and thickness to a thin distal tip;

the head portion having an upper edge defining a downwardly extending depression.

2. The implant defined in claim 1 wherein the head portion has a lower edge which extends upwardly to merge with the tapering tail portion, and the upper edge of the head portion extends mesially upwardly from the depression, and then downwardly to merge with the tail portion, the downward angulation of the upper edge being greater than the upward angulation of the lower edge.

3. The implant defined in claim 2 wherein the elongated concave rear surface of the strip is generally flattened in transverse cross section, the elongated concave rear surface having a substantially constant cylindrical radius with respect to a transverse axis with the exception of a portion extending mesially from the general area of the upper-edge depression which is of increasing cylindrical radius.

4. The implant defined in claim 3 wherein the head portion defines a pair of spaced-apart holes therethrough for suture anchorage.

5. An implant for facial augmentation by surgical submalar placement against a maxillary canine fossa to extend rearwardly beneath a zygomatic arch of a patient's skeletal bone structure, the implant comprising an integrally molded and elongated curved strip having a convex front surface and a concave rear surface, the front surface being generally convex in cross section;

the strip having an enlarged head portion configured to seat in the canine fossa, and an integrally formed tail portion extending laterally and rearwardly from the head portion to a distal tip, the tail portion tapering in cross-sectional thickness and height toward the distal tip;

the head portion having an upper edge defining a downwardly extending depression to accommodate an infraorbital nerve beneath which the implant is to be positioned.

6. The implant of claim 5 wherein the strip has an arc length in the range of about 1⅜ inches to 2¾ inches, a maximum cross-section height in the range of about 0.3 inch to 0.9 inch, and a maximum cross-sectional thickness in the range of about 0.10 inch to 0.25 inch.

* * * * *